United States Patent
Prestel

(10) Patent No.: US 6,752,823 B2
(45) Date of Patent: Jun. 22, 2004

(54) SURGICAL FORCEPS

(75) Inventor: Stephan Prestel, Rheinstetten-Mörsch (DE)

(73) Assignee: Richard Wolf GmbH, Knittlingen (DE)

( * ) Notice: Subject to any disclaimer, the term of this patent is extended or adjusted under 35 U.S.C. 154(b) by 193 days.

(21) Appl. No.: 10/086,264

(22) Filed: Mar. 1, 2002

(65) Prior Publication Data

US 2002/0123767 A1 Sep. 5, 2002

(30) Foreign Application Priority Data

Mar. 2, 2001 (DE) .......................... 101 10 106

(51) Int. Cl.[7] .......................... A61B 17/28; A61B 17/42; A61B 17/44
(52) U.S. Cl. .......................... 606/208; 606/205; 606/210
(58) Field of Search .......................... 606/83, 170, 182, 606/205, 206, 207, 208, 209, 210

(56) References Cited

U.S. PATENT DOCUMENTS

| | | | |
|---|---|---|---|
| 5,009,661 A | | 4/1991 | Michelson .................. 606/170 |
| 5,439,473 A | * | 8/1995 | Jorgensen .................. 606/182 |
| 5,556,370 A | * | 9/1996 | Maynard .................... 600/151 |
| 5,562,699 A | | 10/1996 | Heimberger ................ 606/205 |
| 5,628,765 A | | 5/1997 | Morita ....................... 606/182 |
| 6,071,299 A | | 6/2000 | Dingler et al. .............. 606/170 |

FOREIGN PATENT DOCUMENTS

| | | | |
|---|---|---|---|
| DE | 36 01 166 C2 | 7/1987 | ........... A61B/17/28 |
| DE | 36 01 166 | 7/1987 | ........... A61B/17/28 |
| DE | 298 06 799 | 6/1998 | ........... A61B/17/28 |
| DE | 197 13 067 | 10/1998 | ........... A61B/17/32 |
| DE | 197 23 637 | 11/1998 | ......... A61B/17/122 |
| DE | 299 17 554 U1 | 12/1999 | ........... A61B/17/00 |
| DE | 299 17 554 | 12/1999 | ........... A61B/17/00 |
| EP | 0 674 878 | 3/1995 | ........... A61B/17/28 |

* cited by examiner

Primary Examiner—Julian W. Woo
Assistant Examiner—Charles H. Sam
(74) Attorney, Agent, or Firm—Cohen, Pontani, Lieberman & Pavane

(57) ABSTRACT

A surgical forceps includes a forceps jaw, with a handle consisting of two grip parts with which the one first grip part is connected to a forceps housing and the other second grip part is pivotable for opening and closing the jaw mouth, with an adjustment rod which is distally and proximally adjustable for opening and closing the jaw mouth and whose proximal end has a connection to a limb of the two limbed second grip part, and with at least one would spring element as an overload protection against the breakage of jaw parts. A particularly effective overload protection, a simple forceps construction and a small constructional size of the forceps are achieved according to the invention in that the spring element consists of a flat material wound in a serpentine manner with windings lying in one plane.

22 Claims, 8 Drawing Sheets

SURGICAL FORCEPS

BACKGROUND OF THE INVENTION

1. Field of the Invention

The invention relates to a surgical forceps with a forceps jaw, with a handle consisting of two grip parts with which the one first grip part is connected to a forceps housing and the other second grip part is pivotable for opening and closing the jaw mouth, with an adjustment rod which is distally and proximally adjustable for opening and closing the forceps jaw and whose proximal end has a connection to a limb of the two-limbed second grip part, and with at least one wound spring element as an overload protection against the breakage of jaw parts.

2. Description of the Prior Art

In order for example with the excision of samples to be able to securely grasp tissue and to separate this cleanly from the remaining tissue, high forces must be transmited onto the cutting edges of the jaw parts of a surgical forceps. With a pressure of the jaw parts which is too slight the tissue is not correctly separated which may lead to the fact that incompletely separated tissue may be torn off. With a pressure on the jaw parts which is too great—brought about via the handle of the forceps—there exists the danger that parts of the forceps may break. In both cases there therefore exists the danger that the patient is endangered or is injured. For the unexperienced operator it is also difficult to meter the required force on the grip part so that on the one hand the tissue is cleanly severed, but that on the other hand the forceps is not damaged.

DE 36 01 166 C2 and DE 299 17 554 U1 disclose therefore in each case a surgical forceps of the known type with which the transmission of the force exerted on the handle is effected via a spring integrated into the forceps in the form of a helical spring. The forceps is thus secured from overload.

With a surgical forceps according to DE 299 17 554 U1 it is however disadvantageous that the spiral spring provided here must have a large construction, i.e. a large diameter and a great length in order to achieve the desired overload securement. With this inevitably the size and the weight of the forceps increases. Furthermore with this forceps it is provided that with a loading the whole forceps shank with the jaw part displaces in the direction of the jaw part which is not favorable for the positioning of the jaw part. Furthermore this forceps comprises a multitude of individual components which is why it is expensive.

The solution according to DE 36 01 166 C2 has to the same extent a large construction and on account of design by way of the overload securement has a great length which in the same manner leads to difficulty in handling.

Another surgical instrument known from DE 298 06 799 U1 as an overlaod protection applies a buffer consisting of rubber elastic material which is shaped in an annular manner and is installed into a hollow-cylindrical holder. With this although a smaller and lighter construction is possible it is however disadvantageous here that the buffer of elastic material may age by which means its spring property is lowered. Furthermore there also arise problems with the cleaning and sterilization of the forceps since the region of the buffer is difficultly accessible.

BRIEF SUMMARY OF THE INVENTION

It is therefore the object of the invention to further develop a surgical forceps of the initially mentioned type such that the mentioned disadvantages are avoided, in particular by way of a special design of the spring element or spring elements and its or their arrangement. The forceps is thus to have as small and as compact as possible construction and not be significantly heavier than previously known forceps without overload protection. The parts of the overload securement are to be easy to clean and sterilise. The forceps concept is further to be able to be simply adaptable to the various demands of the effect of the overload securement. Finally the construction of the forceps is to be simpler than is the case with the state of the art so that also the manufacturing costs for the forceps may be reduced.

The solution of this object of the invention is characterized in that the spring element consists of a flat serpentine-shaped material with windings lying in one plane. In contrast to the state of the art thus there is provided in principle a different construction of the spring element.

Preferably the spring element connects one limb of the second grip part directly to the proximal end of the adjusting rod. At the same time the forceps may be designed such that alternatively in the case of overload the spring element acts as a tension spring or as a compression spring.

It may also be provided that the forceps jaw is opened against the effect of a compression spring located in the forceps housing, wherein the compression spring which is formed as a helical spring and which runs through the adjusting rod is arranged in a sleeve adjustable axially in the forceps housing on pivoting the second grip part, and which with its one end is supported on the base of the sleeve open at one end and with its other end is supported on a shoulder in the forceps housing.

A particularly simple construction results when the two ends of the spring element in each case are formed as a knuckle eye, wherein the knuckle eyes in each case are connected byway of a joint pin on the one hand to the adjusting rod and on the other hand to the limb of the second grip part.

The respective neighbouring limbs of the spring element windings may run parallel or diverge in the direction of the connection webs connecting them or converge in the direction of the free space of the winding.

An influencing of the spring stiffness may be achieved in that there are connected at least two spring elements in parallel and arranged next to one another with knuckle eyes flush at their ends. The danger of the jamming of a finger in the spring elements is avoided in that in this case two windings of a spring element in relation to the windings of the spring element arranged next to it run displaced by half the width of a winding.

The spring elements may be easily assembled and dismantled when in the forceps housing and in the limb of the second grip part there are provided recesses open at the top for accommodating the spring elements.

The spring elements consist e.g. of spring steel, in particular of a TiNi alloy. With regard to the manufacturing possibility it is to be noticed that a simple and economic manufacture is given when the spring elements are either manufactured with the laser cutting method, by punching or with the erosion method, wherein a metal plate of initial material is used.

BRIEF DESCRIPTION OF THE DRAWINGS

In the drawings there are shown embodiment examples of the invention. There are shown in.

DETAILED DESCRIPTION OF THE INVENTION

Figure 1:
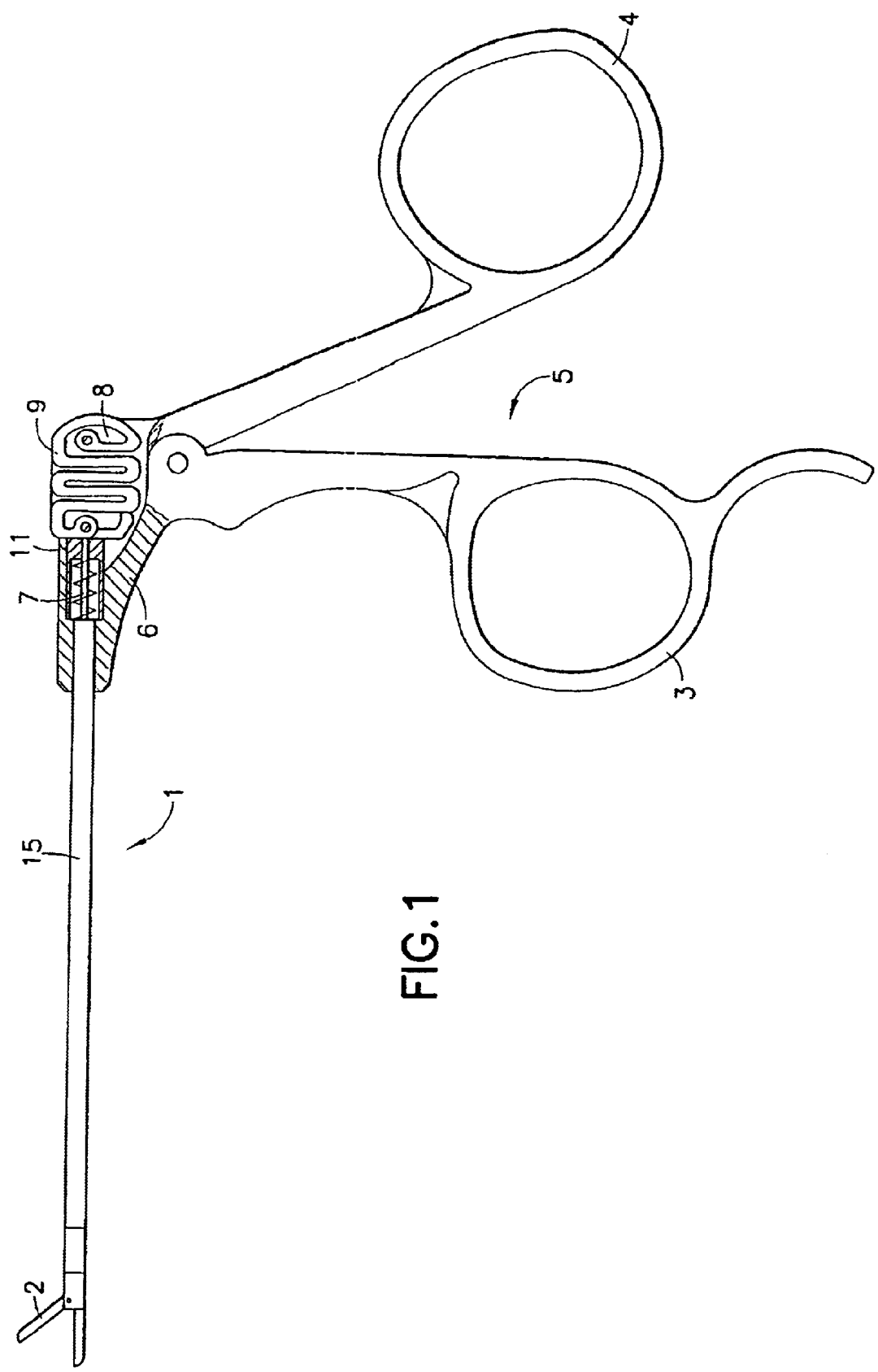
FIG. 1 is a lateral view of a surgical forceps according to a first embodiment of the present invention with an opened forceps jaw.

In FIG. 1 there is to be recognized a surgical forceps 1 which comprises a forceps jaw 2 which by actuation of one of the two grips 3 and 4 of a handle 5 may be opened and closed in a manner known per se. The first grip part 3 is rigidly fastened on a forceps housing 6 whilst the second grip part 4 is pivotably mounted in a jointed manner on the forceps housing 6. The forceps low is attached on the distal end region of a shank 15 designed in a tubular manner. In the shank 15 there is arranged an adjusting rod 7 in an axially displaceable manner. Its axial displacement movement on account of an actuation of the handle effects in the usual manner the opening and t he closing of the forceps jaw 2.

The proximal end of the adjusting rod 7 is in direct contact with the limb 8 of the second grip part 4. For effecting the overload protection the connection between the proximal end of the adjusting rod 7 and the limb 8 is created by a spring element 9. This consists of a flat serpentine-shaped material, wherein the windings of the element 9 lie in a plane, in the case of FIG. 1, in the plane of the drawing.

Figure 2:
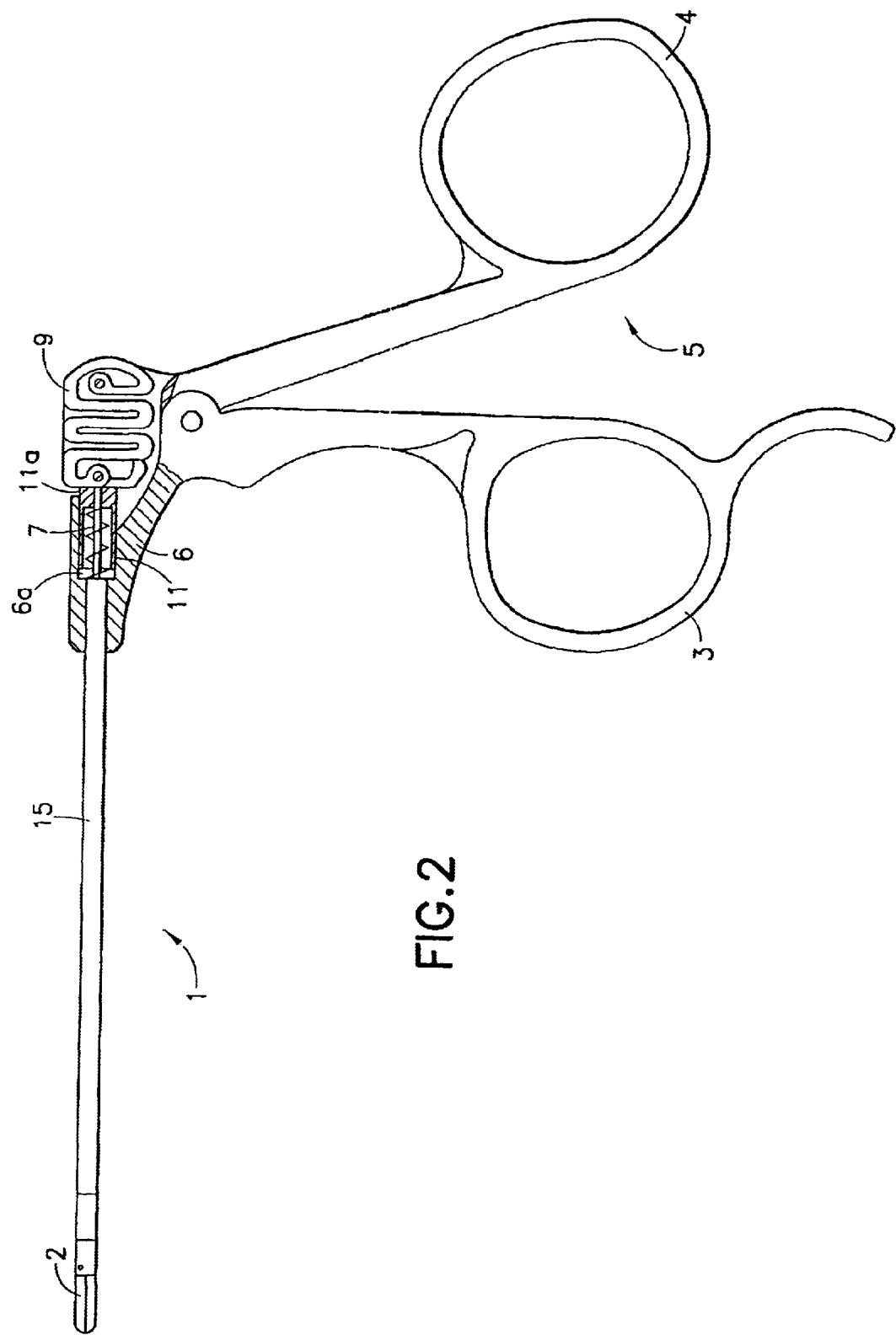
FIG. 2 is a lateral view of the surgical forceps according to FIG. 1 with a closed forceps jaw.

The comparison of FIG. 1 with FIG. 2 shows the manner of acting of the spring element 9. Whilst the forceps 1 in FIG. 1 is to be seen with an opened forceps jaw 2, this is closed in FIG. 2. By way of pivoting the second grip part 4 in the clockwise direction for closing the forceps jaw 2 the spring element 9 is loaded in tension. The tension force is transmitted via the adjusting rod 7 which with this moves proximally, onto the pivotingly movable jaw part of the forceps jaw 6.

Also with an increased actuation of the handle 5 this does not lead to a destruction of the forceps 1, since excess actuation forces are avoided by the spring element 9 since the spring element with this is extended and accommodates a part of the forces. Such a deformation of the spring element is effected for the protection of the forceps always when between the two jaw part limbs there is located for example an object to be grasped, such as e.g. tissue or bone part, and the two grip parts 3, 4 of the handle 5 are excessively pressed together.

The jaw mouth 2 may be opened against the effect of a compression spring which is located in the forceps housing 6 and is shown schematically in FIGS. 1 and 2. The compression spring formed as a helical spring and which is run through by the adjusting rod 7 is arranged in a sleeve 11 adjustable axially in the rod housing on pivoting the grip part 4, and is supported with its one end on the base 11a of the sleeve 11 open at one end and with its other end is supported on a shoulder 6a in the forceps housing 6 (FIG. 2).

Figure 3:
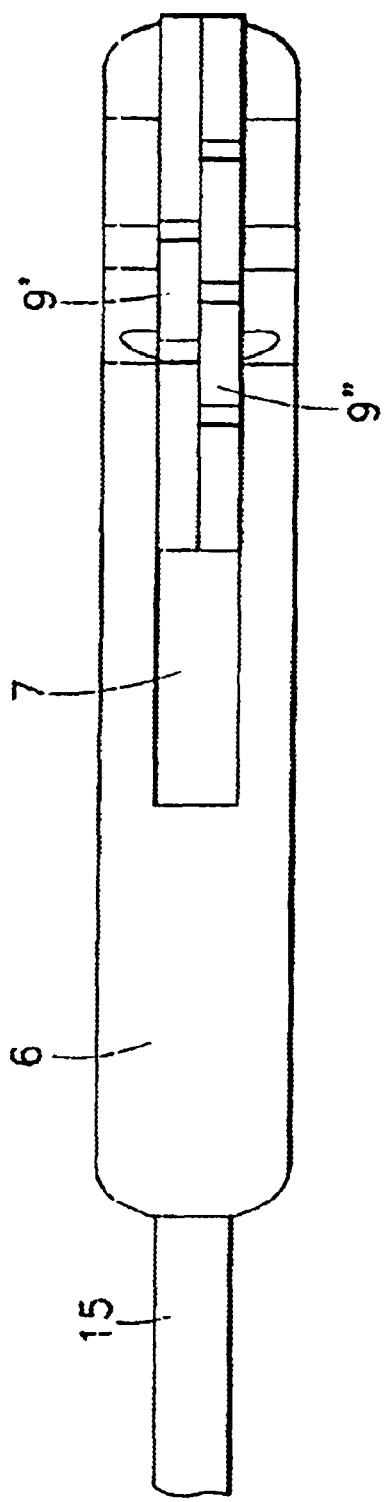
FIG. 3 is a plan view of the region of the spring elements of the forceps of FIG. 1.

As can be seen in FIG. 3 here there are arranged two spring elements 9' and 9" connected parallel next to one another. The whole spring stiffness is thus doubled in comparison to a design with only one spring according to the FIGS. 1 and 2.

Figure 4:
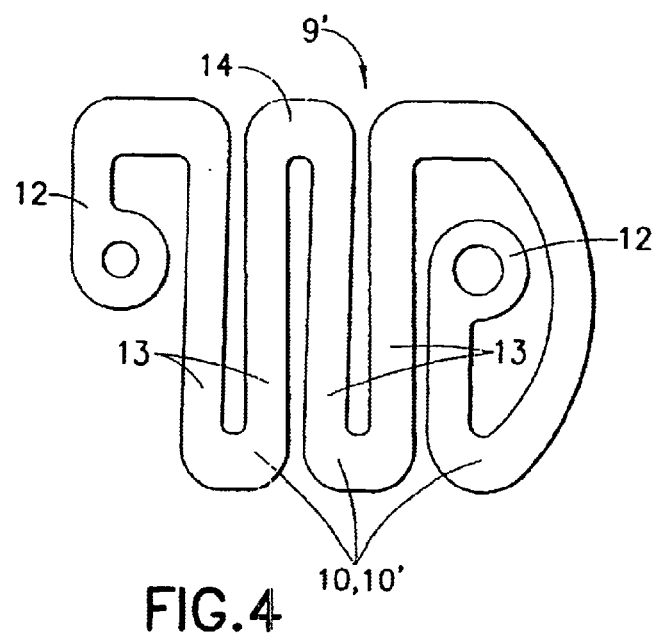
FIG. 4 is a lateral view of a first spring element of the spring elements in FIG. 3.
Figure 5:
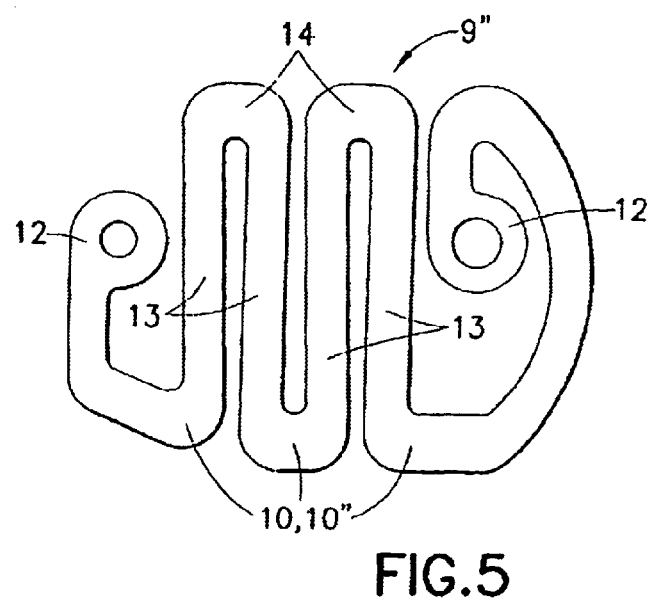
FIG. 5 is a lateral view of a second spring element of the spring elements in FIG. 3.
Figure 6:
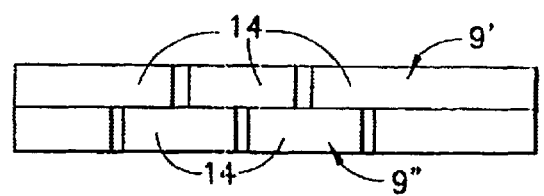
FIG. 6 is a plan view of the two spring elements of FIG. 3 joined next to one another.

Details of this are shown in FIGS. 4, 5 and 6. The spring elements 9' and 9" consist in each case of a number of windings 10, 10' or 10, 10". The windings have limbs 13 which above and below are connected to winding webs 14. The respective ends of the spring elements 9, 9', 9" are provided with knuckle eyes 12. The respective ends of the spring elements 9, 9', 9" in each case with one pin to be inserted through in each case one knuckle eye may be releasably connected to the proximal end of the adjusting rod 7 and to the limb 8 of the second grip part 4. The pins at the same time also engage through corresponding bores in the adjusting rod 7 or in the limb 8.

Both spring elements 9' and 9" are assembled next to one another. As is to be deduced from FIG. 6 both elements 9' and 9" are designed such that the windings 10' of the one spring element 9' in relation to the windings 10" of the spring element 9" arranged next to it run displaced by half the width of a winding. With this there results as a whole a largely closed surface of the spring assembly by which means it is ensured that a jamming in for example of a finger of the operator on actuation of the forceps is ruled out.

So that the spring elements 9' and 9" installed between the adjusting rod 7 and the limb 8 project as little as possible out of the upper bordering of the forceps housing 6 the knuckle eyes 12 provided for receiving joint pins, with respect to the longitudinal middle axis of the one spring element 9', are arranged displaced with respect to those of the other spring element 9", as becomes clear with a comparison of FIGS. 4 and 5. Both spring elements 9' and 9' are thus not formed mirror symmetrical to the common longitudinal middle axis.

As may further be deduced from FIGS. 4 and 5 in each case neighbouring limbs 13 of the windings 10, 10', 10" diverge in the direction of the winding web 14 connecting them or converge in the direction of the winding free space, by which means different than with a likewise practicable parallel course of the limbs a relatively small length of the spring elements may be achieved with a large spring path despite this.

By way of a suitable design of the individual winding of the spring element 9, 9', 9", thus by way of the suitable selection of the dimensions of length, width and thickness of the windings, but also by way of a suitable material selection, the spring constant of the spring elements 9', 9" may be influenced and adapted to the desired case of application.

The parallel arrangement of several spring elements as well as the influencing of the spring constant of an individual spring element by way of modifications of the geometry permit thus a directed influencing of the whole spring stiffness and thus the effect of the overload securement. This represents an enormous advantage with respect to known forceps.

Figure 7:
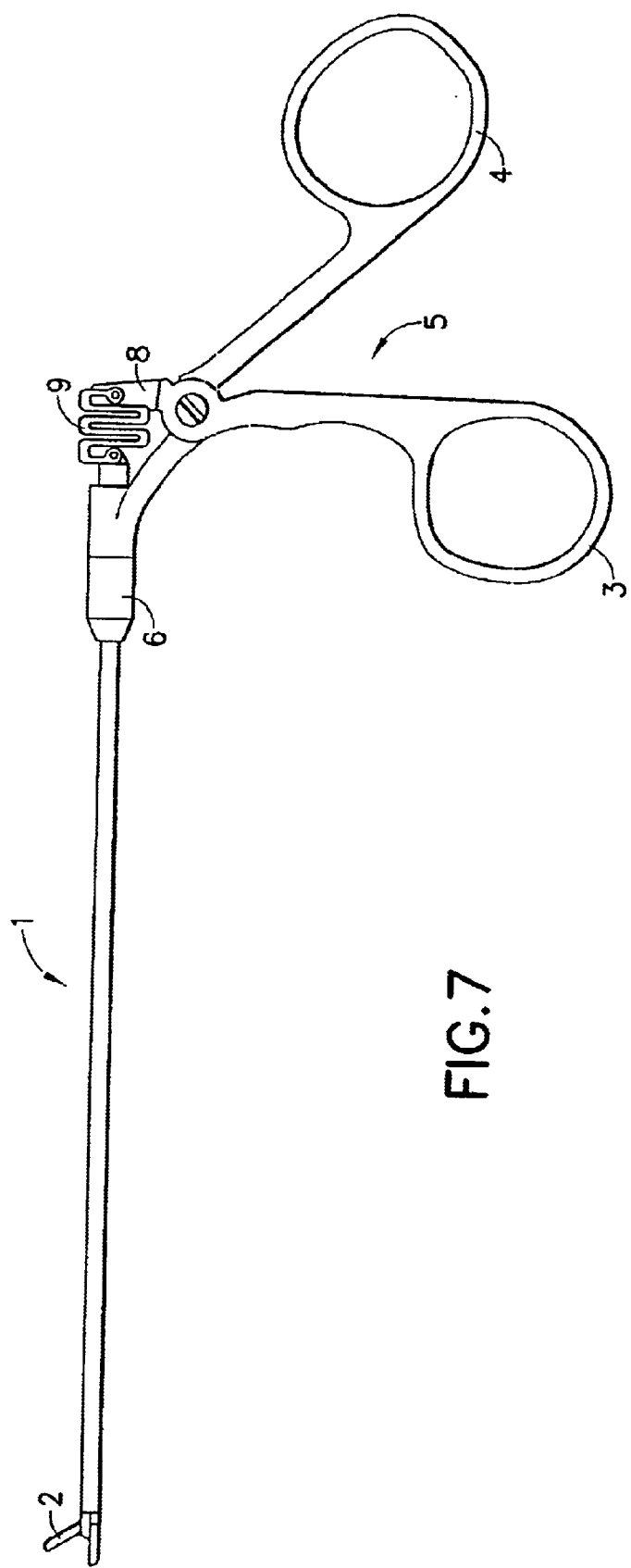
FIG. 7 is a lateral view of a forceps according to a second embodiment of the present invention with a spring element with an opened forceps jaw.
Figure 8:
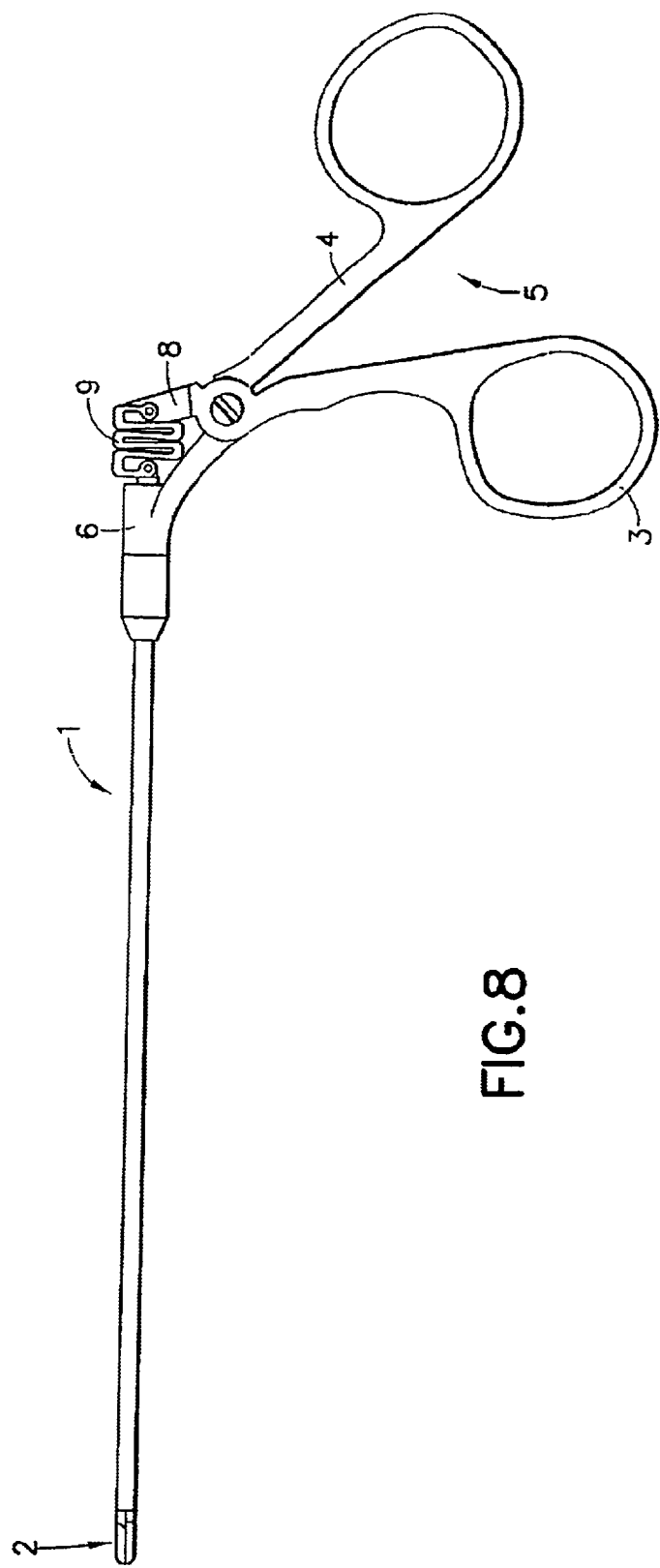
FIG. 8 is a lateral view of the forceps according to FIG. 7 with a closed forceps jaw.
Figure 9:
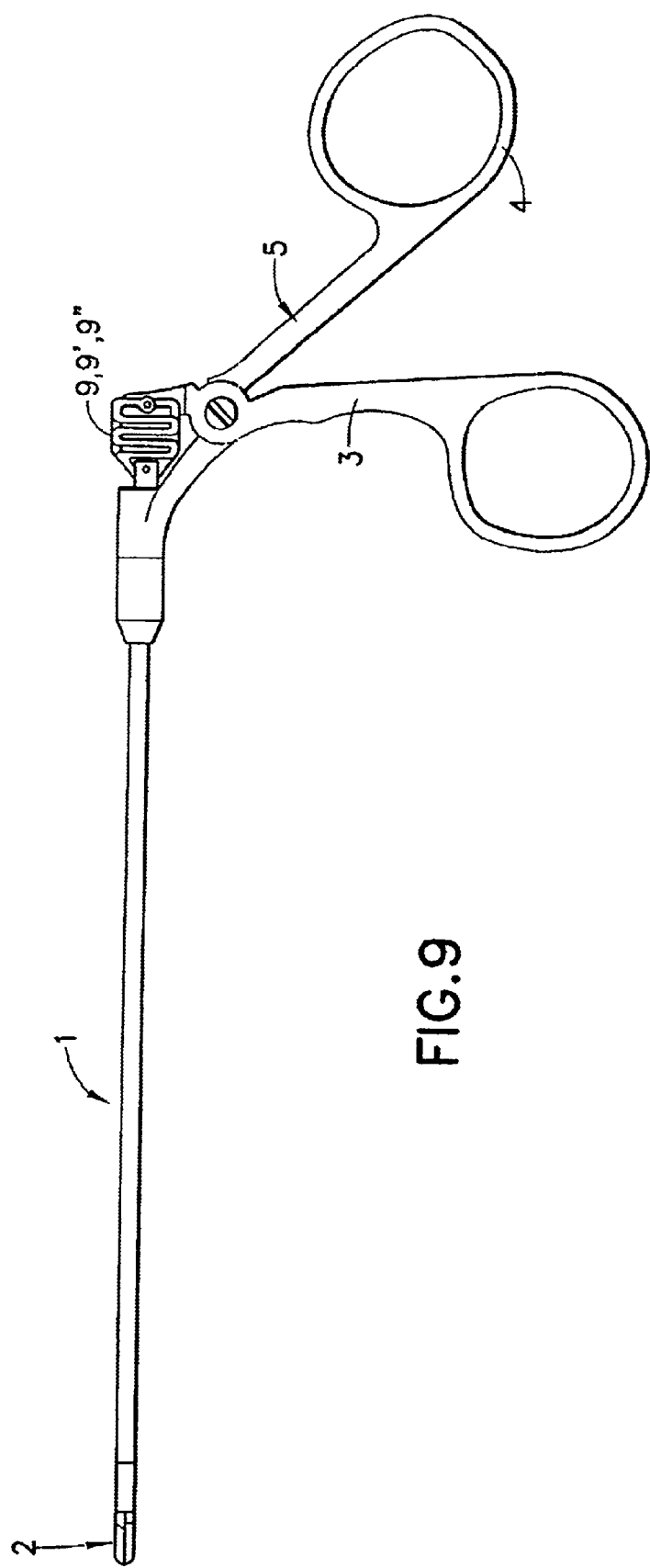
FIG. 9 is a lateral view of the forceps according to FIG. 8 with two spring elements.

In FIG. 7 there is shown an alternative embodiment form of the forceps 1. Whilst with the embodiment example according to the FIGS. 1 to 6 it is envisaged that the spring element 9 on actuation of the forceps 1, thus on closing the forceps jaw 2 is loaded in tension, with the formation according to FIG. 7 it is such that the spring element 9 in this case is loaded in compression. The comparison of FIG. 7 with FIG. 8 which shows the forceps 1 with a closed forceps jaw 2 makes clear that the spring element 9 is from now on pressed together. According to FIG. 9 also two or more spring elements 9', 9" arranged in parallel may be used on closing the forceps jaw loaded in compression.

Figure 10:
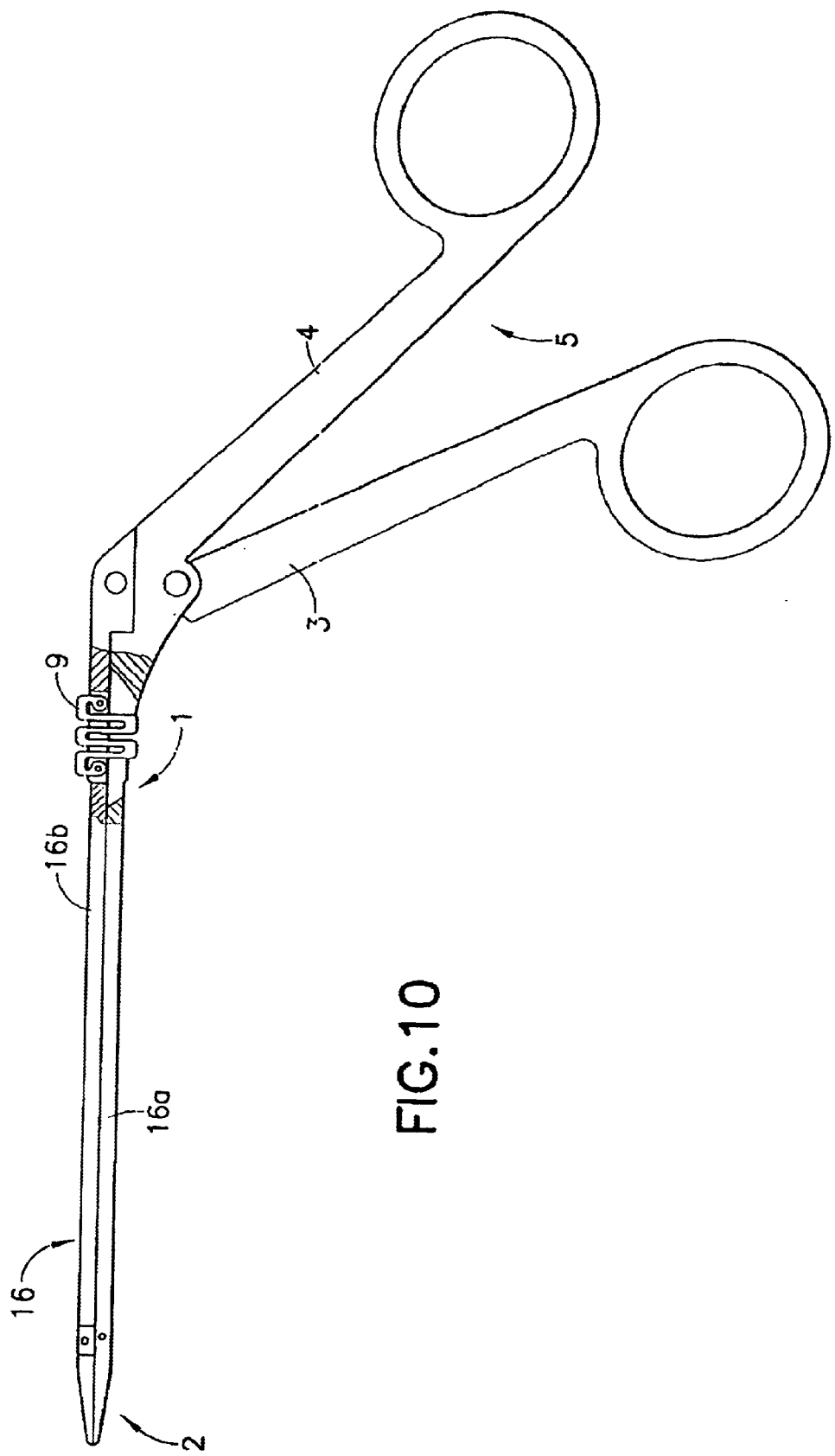
FIG. 10 is a lateral view of a third embodiment of a surgical forceps designed as a rail shank forceps.

The concept according to the invention may also be applied to other forceps types. FIG. 10 for example shows a rail shaft forceps. This comprises a two-part longitudinally divided shank 16, wherein a shank part 16a is stationary and the other shank part 16b acting as an adjusting rod may be axially adjusted by actuation of the handle 5 for opening or closing the jaw part 2. Also in this forceps as an overlooked protection there is integrated a spring element 9 which is in connection on the one hand with the proximal end of the shank part 16b and with the pivotable grip part of the handle on the other hand.

Although in the embodiment examples according to the FIGS. 1 to 9 the spring elements are constantly arranged in a proximally situated space above the handle, it is also possible to accommodate them at another location of the forceps, for example in the inside of the forceps shank or in a space in the distal end region of the forceps housing.

What is claimed is:

1. A surgical forceps, comprising:
   a forceps housing;
   a forceps jaw having a jaw mouth;
   a handle having a first grip part connected to said forceps housing and a second grip part pivotably connected to said forceps housing and being pivotable for opening and closing said jaw mouth, said second grip part having a limb;
   an adjustment rod having a distal end and a proximal end and being distally and proximally adjustable for opening and closing said jaw mouth, wherein said proximal end of said adjustment rod is connected to said limb of said second grip part; and
   at least one spring element arranged in a force path between said second grip part and said forceps jaw for providing overload protection against breakage of said jaw parts, wherein said at least one spring comprises a flat serpentine-shaped material with windings lying along one plane.

2. The surgical forceps of claim 1, wherein said at least one spring element is connected between said limb of said second grip part and said proximal end of said adjustment rod.

3. The surgical forceps of claim 2, wherein said at least one spring is tensioned during an overload of said forceps jaw.

4. The surgical forceps of claim 1, wherein said at least one spring is tensioned during an overload of said forceps jaw.

5. The surgical forceps of claim 1, wherein said at least one spring is compressed during an overload of said forceps jaw.

6. The surgical forceps of claim 2, wherein said at least one spring is compressed during an overload of said forceps jaw.

7. The surgical forceps of claim 1, further comprising a compression spring arranged in said forceps housing such that said jaw forceps jaw is opened against a force of said compression spring.

8. The surgical forceps of claim 7, wherein said compression spring comprises a helical spring arranged in a sleeve defined in said forceps housing, wherein one end of said sleeve comprises a base adjustable in response to a pivoting of said second grip part, said helical spring including one end supported on said forceps housing and another end supported on said base.

9. The surgical forceps of claim 1, further comprising joint pins connected to said adjustment rod and said limb of said second grip part, wherein said at least one spring element comprises two ends and a knuckle eye formed at each of said two ends of said at least one spring and said joint pins are respectively received in said knuckle eyes for connecting said adjustment rod to said limb of said second grip part.

10. The surgical forceps of claim 7, further comprising joint pins connected to said adjustment rod and said limb of said second grip part, wherein said at least one spring element comprises two ends and a knuckle eye formed at each of said two ends of said at least one spring and said joint pins are respectively received in said knuckle eyes for connecting said adjustment rod to said limb of said second grip part.

11. The surgical forceps of claim 1, wherein said windings of said at least one spring element include limbs connected by webs, thereby defining a free space in the windings, and wherein adjacent ones of said limbs of said at least one spring element diverge or converge toward said free space.

12. The surgical forceps of claim 1, wherein said at least one spring element comprises at least two spring elements connected in parallel.

13. The surgical forceps of claim 12, further comprising joint pins connected to said adjustment rod and said limb of said second grip part, wherein said at least two spring element each comprise two ends and a knuckle eye formed at each of said two ends of said at least two spring elements and said joint pins are respectively received in said knuckle eyes for connecting said adjustment rod to said limb of said second grip part.

14. The surgical forceps of claim 7, further comprising joint pins connected to said adjustment rod and said limb of said second grip part, wherein said at least one spring element comprises at least two spring elements connected in parallel and each of said at least two spring elements comprises two ends and a knuckle eye formed at each of said two ends, said joint pins being respectively received in said knuckle eyes for connecting said adjustment rod to said limb of said second grip part.

15. The surgical forceps of claim 12, wherein said windings of said at least two spring elements include limbs connected by webs, thereby defining a free space in the windings between each pair of adjacent limbs, and wherein adjacent ones of said limbs of said at least one spring element diverge or converge toward said free space.

16. The surgical forceps of claim 12, wherein said windings of a first spring element of said at least two spring elements are offset relative to said windings of a second spring element of said at least two spring element arranged directly adjacent to said first spring element by one half of a width of said windings.

17. The surgical forceps of claim 1, wherein recesses are defined in said forceps housing and said limb of said second grip part for receiving said at least one spring element.

18. The surgical forceps of claim 1, wherein said at least one spring element is made of a material comprising spring steel.

19. The surgical forceps of claim 1, wherein said at least one spring element is made of a material comprising a TiNi alloy.

20. The surgical forceps of claim 1, wherein said at least one spring element is cut from a metal plate using a laser cutting method.

21. The surgical forceps of claim 1, wherein said at least one spring element is punched from a metal plate.

22. The surgical forceps of claim 1, wherein said at least one spring element is made from a metal plate using an erosion method.

* * * * *